United States Patent

James

Patent Number: 5,374,380
Date of Patent: Dec. 20, 1994

[54] SALINITY CONTROL OF SUMP WATER USING CONDUCTIVITY PROBES

[75] Inventor: Robert W. James, Crafers, Australia

[73] Assignee: F F Seely Nominees Pty Ltd., Australia

[21] Appl. No.: 996,119

[22] Filed: Dec. 23, 1992

[51] Int. Cl.$^5$ ............................................. F25B 39/02
[52] U.S. Cl. ........................................ 261/26; 62/171;
    137/93; 261/DIG. 46; 324/439; 324/446
[58] Field of Search ................. 210/96.1, 138; 261/26,
    261/DIG. 41, DIG. 46, 97; 62/171; 137/93;
    324/439, 446, 448, 442

[56] References Cited

U.S. PATENT DOCUMENTS

| | | | |
|---|---|---|---|
| 3,188,561 | 6/1965 | Ingram | 324/439 |
| 3,361,150 | 1/1968 | Horner | 210/96.1 |
| 3,592,212 | 7/1971 | Schleimer et al. | 261/DIG. 46 |
| 4,192,832 | 3/1980 | Goettl | 261/DIG. 46 |
| 4,273,146 | 6/1981 | Johnson | 137/93 |
| 4,507,521 | 3/1985 | Goellner | 324/448 |
| 4,576,013 | 3/1986 | Sperr et al. | 261/DIG. 46 |
| 4,833,413 | 5/1989 | Head | 324/446 |
| 5,084,217 | 1/1992 | Dodds | 261/97 |
| 5,192,464 | 3/1993 | Pawlowski et al. | 261/DIG. 46 |

FOREIGN PATENT DOCUMENTS 593056  2/1986  Australia ............................... 261/26

OTHER PUBLICATIONS

Munters' brochure, containing product specification and performance data for CELdek/COOLdek, pp. 20-21, date unknown.

Primary Examiner—Joseph W. Drodge
Attorney, Agent, or Firm—Brown, Martin, Haller & McClain

[57] ABSTRACT

Salinity control of sump water in an evaporative cooler (10) wherein a pump (19) continuously impels a water flow from a sump (11) to an evaporative surface where some of the water is evaporated by air flow from a fan (15, 16). Control is affected by sensing electrical resistance of the sump water with monel probes (36) energised with low voltage alternating current, and initiating an "ON" period of a timer (quad NOR gate) when resistance drops below a preset level. During the "ON" period a solenoid valve (25) is opened in a bleed line and some only of the pumped sump water is passed to drain, without interruption of cooler operation.

6 Claims, 3 Drawing Sheets

SALINITY CONTROL OF SUMP WATER USING CONDUCTIVITY PROBES

This invention relates to salinity control of sump water of an evaporative device, and is particularly applicable to an evaporative cooler having a sump wherein the sump water is recirculated and evaporated in a pad for example, but as a result, the salinity in the sump rises to unacceptable levels.

BACKGROUND OF THE INVENTION

The conventional evaporative cooler constantly replenishes water from a water supply when in operation, through a float valve in the sump, to make up for water loss due to evaporation in the airstream. The incoming water always contains a small concentration of salt dissolved in it. If no means are provided to remove that salt, it will concentrate in the sump of the cooler, since only pure water is evaporated into the airstream.

Concentration of salt, if allowed to become too high, has several detrimental effects including:

a) crusting of the salt on pads, lowering their effectiveness and decreasing their life;
b) decreasing the performance of the cooler by reducing evaporation rate;
c) providing tracking paths which enable leakage from the cooler to take place; and
d) increasing corrosion rate on the vulnerable components which are subject to corrosion.

These problems have been well recognised and traditional methods of controlling salt concentration include allowing bleeding of the water, or periodically actuating a dump valve to dump the tank or sump to drain. However these methods drain much more water to the drain than is actually required for salt control, thereby wasting water and adding to the operating cost of the cooler. This is a matter of considerable importance in arid areas where water is scarce.

The most relevant art otherwise known to the Applicant is disclosed in a brochure produced by Munters (Aust) Pty Ltd, of Cheltenham, Victoria, Australia, which discloses a conductivity controller in an evaporative cooling system wherein conductivity (a function of total dissolved solids) is continuously measured, and upon passing a set point, opens a solenoid valve and bleeds off system water until it is back within control range. Although the concept is simple, the structural features of such an arrangement discloses three valves in addition to a solenoid valve in a bleed line, and a separate by pass sample line which includes a conductivity probe assembly.

One object of this invention therefore is to provide a mechanically simple device which will effectively bleed off sump water from a cooling system to maintain an acceptably low salinity within the sump, and this is achieved primarily by use of resistance sensing probes which, upon salinity increase, initiate a timer which operates a solenoid valve to effect bleed-off, without interrupting cooler operation.

BRIEF SUMMARY OF THE INVENTION

The invention relates to salinity control of sump water in an evaporative cooler wherein a pump continuously impels a water flow from a sump to an evaporative surface where some of the water is evaporated by air flow from a fan. Control is effected by sensing electrical resistance of the sump water with special probes and initiating an "ON" period of timer operation when the electrical resistance drops below a preset level. During the "ON" period a solenoid valve is opened in a bleed line and some only of the pumped sump water is by passed to drain, without interruption of the cooler.

It will immediately be seen by those skilled in the art that the cost of the device according to this invention is very small, a very minor part of a cost of an evaporative cooler, but the invention nevertheless automatically effects discharge of the saline water from a cooler or other device once the salinity reaches a level, which can be adjusted, but of course must be below the level wherein the abovementioned difficulties are encountered. The device requires only the addition of probes which may be in the sump, an electronic assembly, a bypass valve, and simple electrical coupling cables and drain hose.

When a timer is used, a relatively constant amount of water is bled from the sump water and this can be so adjusted as to reduce salinity level to an acceptable degree. However, situations may arise when salinity is still sensed to be too high and an embodiment of the invention includes a facility to reinitiate the timer if at the end of an "ON" period the salinity still remains too high.

On the other hand, however, there is a possibility of the time "hunting" and to avoid this possibility the embodiment of the invention described hereunder also has a facility wherein there is a time delay after operating before the timer will recommence its "ON" period, notwithstanding the existence of high salinity.

While the various configurations can be utilised to ensure that there is no interruption of operation of a cooler during bleed off, in an embodiment of the invention, a very simple arrangement is disclosed wherein the electrically actuated drain valve comprises a conduit "T" junction with the upstream limb of the T being connected to the outlet port of the pump, the downstream limb to the evaporative surface and the intermediate limb to the solenoid valve, so that the construction can be exceedingly simple.

If direct current is used for probes, electrolysis may occur, particularly if the probes are continuously energised during operation of the cooler, and to combat this a low voltage alternating current of relatively high frequency can be imparted to the probes and still be used to test the water resistance, and still further the probes can be constituted by monel metal which is noted for its ability to resist corrosion. Furthermore, use of electronic controls allows adjustment of "ON" and "OFF" times by removing or adding links to multiply or divide the preset times. This arrangement allows adjustment of times within normal ranges.

BRIEF DESCRIPTION OF THE DRAWINGS

An embodiment of this invention is described hereunder in some detail with reference to and is illustrated in the accompanying drawings in which.

Evaporative air coolers are produced both in an axial flow fan mode and in a centrifugal fan mode, and this invention is equally applicable to both modes.

Figure 1:
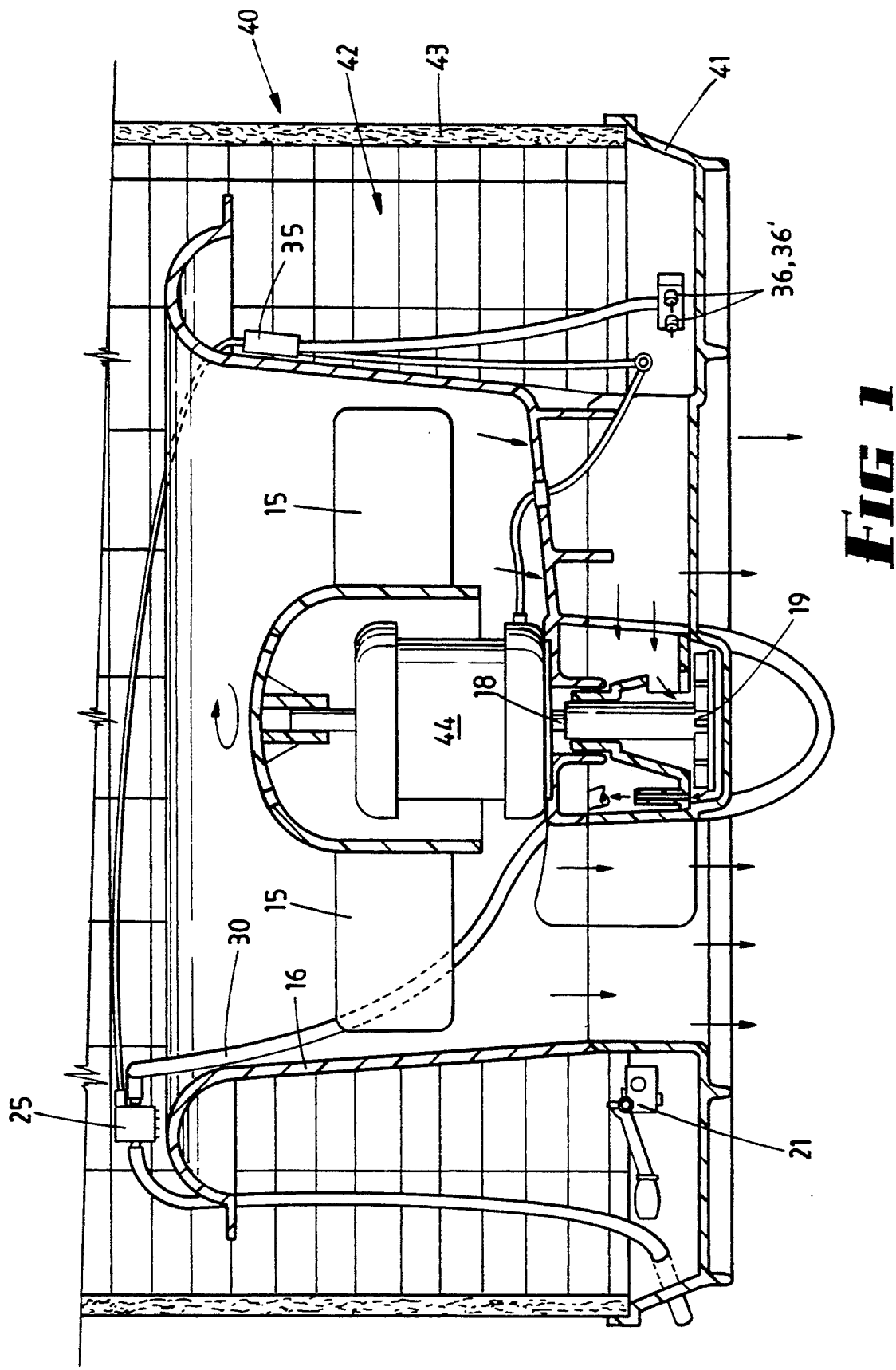
FIG. 1 is a section through portion of a cooler of the type using an axial flow fan, and illustrated in our Australian Patent 593056.

FIG. 1 illustrates an axial flow fan mode arrangement showing the lower portion of an air cooler of the evaporative type, which is described in some detail in our Australian Patent 593056. The cooler 40 is provided with a sump or tank 41 at its lower end, four side walls 42 of grille-like formation each containing a woodwool pad 43, and a motor 44 is coupled to drive a fan having a series of fan glades 15 which rotate within a shroud 16 to cause flow of air (downwards as shown) the air however first having been drawn through the woodwool pads 43.

The lower end of the motor has a downwardly directed shaft 18 which terminates at its lower end in a pump impeller 19 which impels flow of sump water from sump 41 through an output hose 20. The sump water eventually is discharged through the pads 43 in a conventional manner, some of the water being evaporated and the remainder returning to the sump 41. A float valve 21 senses liquid level within the sump and it is replenished when the float of the valve 21 lowers, again in a convention manner.

Figure 2:
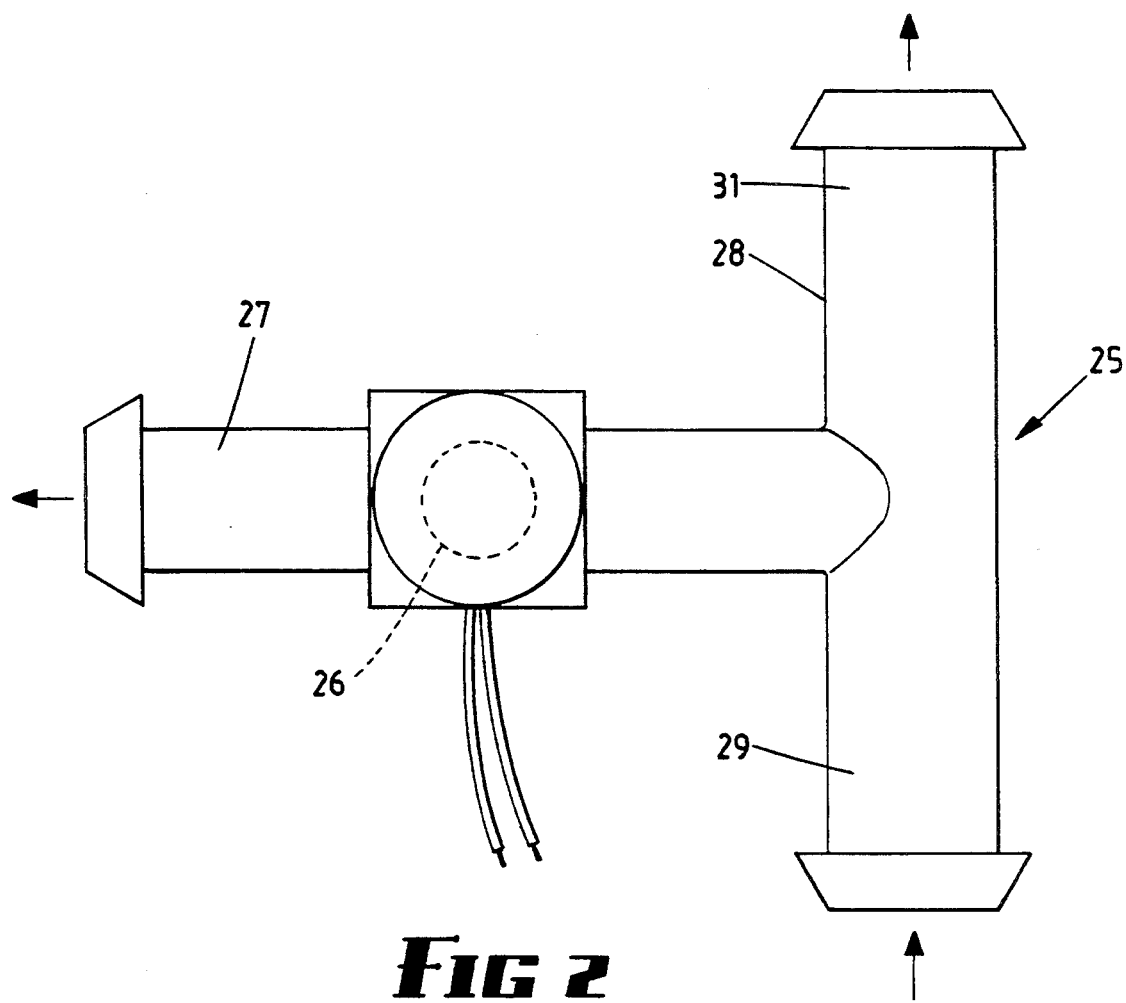
FIG. 2 is a plan view of a solenoid valve assembly.

In order to effect salinity control, it is necessary to periodically bleed some of the sump water from the sump, and this is achieved without interruption of cooler operation by use of a solenoid valve 25 which is shown in more detail in FIG. 2. The solenoid valve 25 comprises a magnetic coil 26 connected in an intermediate limb 27 of a "T" junction 28, the limb 29 being coupled by hose 30 to the outlet of pump 19, and being continuous with the limb 31 which is on the downstream side and extends within the side walls 42 of the cooler to be spread over the upper edges of the pads 43, running down through the pads 43 which provide the necessary evaporative surface for the cooler operation.

With this arrangement, there is a continuous flow of evaporative water to the pads 43 whether or not the solenoid valve is energised by a timer being in its "ON" mode electrical probes 36, 36' are inserted in the sump as illustrated in FIG. 1 and connected to a control circuit 35.

Figure 3:
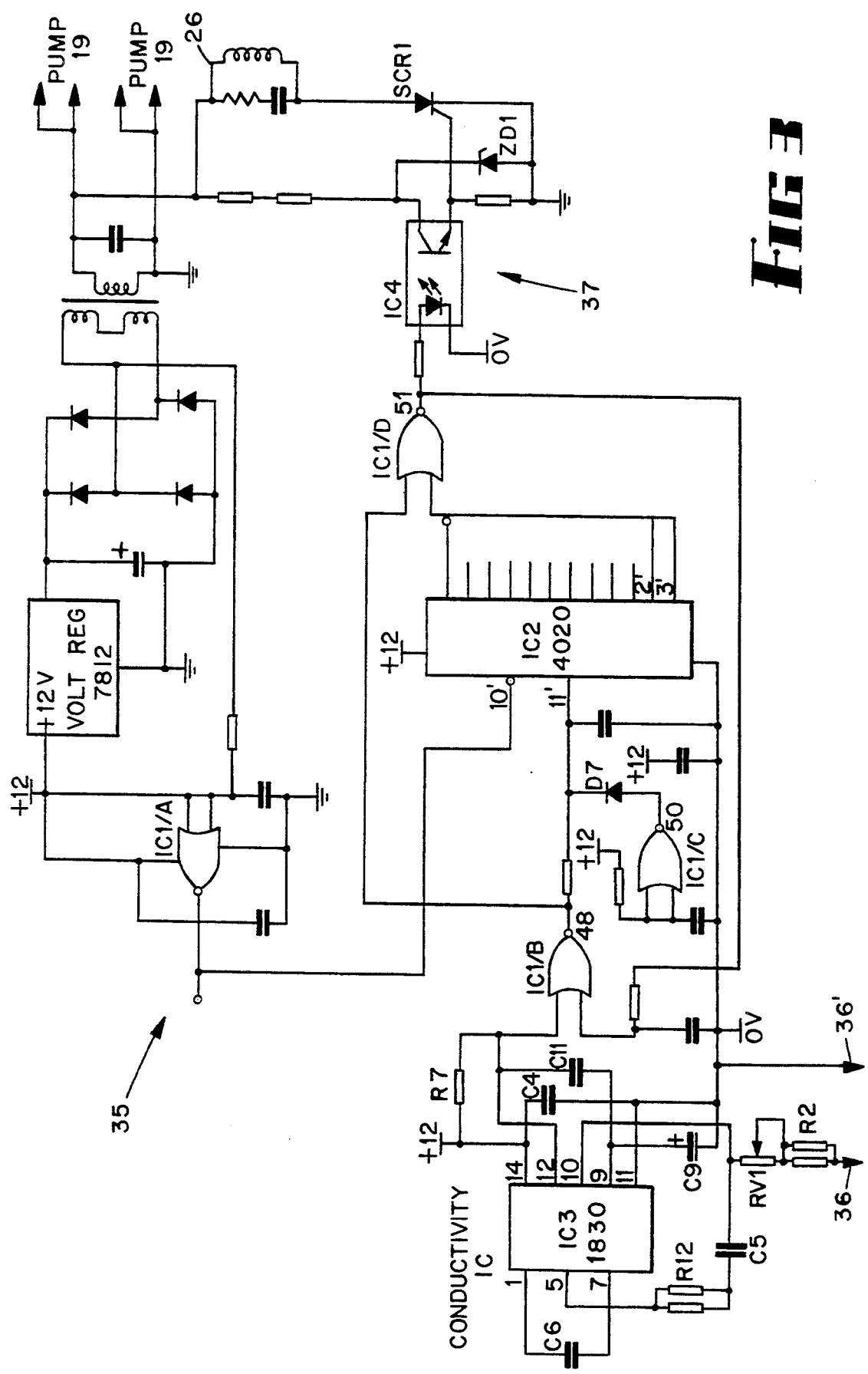
FIG. 3 is a schematic circuit diagram illustrating one means of achieving the electronic control.

It will be obvious to those skilled in the art that alternative control means can be utilised to achieve the required result. FIG. 3 however, shows the preferred arrangement wherein the control circuit 35 includes four logic circuits IC1, IC2, IC3 and IC4. IC1 is a quad NOR gate number 4001 having portions IC1/A, IC1/B, IC1/C and IC1/D connected as illustrated in FIG. 3. IC2 is a timer, IC3 is a conductivity IC, and IC4 is an LED forming part of an opto-isolator 37. The circuit also includes a voltage regulator (7812), and this regulates voltage supplied to conductivity IC3 (1830). Outputs of conductivity IC3 go to portions IC1/B and IC1/C of the 4001 quad NOR gate to the left hand side timer IC2 (4020), and to portion IC1/D to the right hand side of timer IC2, forming part of a driver circuit including opto-isolator 37, and this drives the solenoid coil 26.

The numbers which have been used to designate the voltage regulator (7812), the conductivity IC3, (1830), the timer IC2 (4020), and the IC1 logic circuit (4001); are the numbers which designate these items all of which are readily available. The voltage regulator 7812 provides a 12 volt energy supply for the other three components. One of the probes 36 is connected through potentiometer RV1 and capacitor C5 to pin 5, and also connected to pin 10 of the conductivity IC3, while the other probe 36' is connected to pin 11 of the IC3 (1830). These probes are also shown in FIG. 1, being constituted by two spaced apart monel wires electrically connected to the control circuit 35 which is contained in a box desirably situated well above the sump 41 and in this embodiment on the outside of the shroud 16. It would also be situated most conveniently on the shroud of the centrifugal blower if that type of fan has the invention applied to it.

The conductivity IC3 (1830) responds to the resistance across the probes and the resistor RV1 and is adjusted desirably to a cooler's change of state of conductivity of IC3 when the salinity reaches a preset point which may be adjusted somewhere between 600 and 4000 parts per million. The potentiometers may be replaced by one or two resistors. However, by utilising the capacitor C5 and connecting to pin 5 a very low voltage but relatively high frequency is applied to the probes 36 and this avoids difficulties with corrosion or scale build-up which might otherwise occur if DC is applied. IC3 (1830) has a typical 4.2 volt output between its pins 5 and 11, and an oscillator frequency of 12 kHz for a 0.001 $\mu$Fd capacitor, in the art being a relatively high frequency but very low voltage.

The output of conductivity IC3 is low when the conductivity of the sump water is low, when the output on pin 12 goes high, output 48 of IC1/B goes low, being normally high with both inputs low. This causes IC1/D output 51 to go high and initiates the timer IC2 (4020). When the timer IC2 finishes its "ON" cycle, its output on pin 31 goes high, causing IC1/D output 51 to go low, switching off the LED of the opto-isolator 37. The timer then times for its set period again and then its output on pin 21 goes low. At this point, if the sump salinity is still high, then IC1/B output 48 will still be low and so is the timer pin 21 output, causing IC1/D output 51 to be high, energising the opto-isolator LED again. If the sump water salinity has dropped below the set point, then IC1/B output 48 will be high, causing IC1/D output 51 to remain low. The IC3 (1830) trigger level may be adjusted as follows:

Delete R12 to set for 1000 $\mu$siemens/cm
RV1 provides further adjustment
Delete R2 to set for 2500 $\mu$siemens/cm
(1 minute 21 second is standard)
connect pin 31 of 4020 timer for 2 minutes 43 seconds IC1/C is configured in such a manner that at power-up of the electronic components, its output 50 is high for a short period to inhibit timer operation and IC1/D output 51 from going high. This is used to stop unwanted activation of the solenoid valve 26 at unit switch-on.

When the opto-isolator LED is energised, the transistor switch allows the zener diode ZD1 regulated voltage to be applied across SCR1 gate to neutral, thus triggering SCR1 to provide a current path for the operation of the solenoid valve 26.

Capacitor C6 is connected between pins 3 and 7 of IC3. Capacitor C9 is connected to pin 9. Capacitor C4 is connected to pin 4. Capacitor C11 is connected between pins 2 and 9. Output line 48 is connected to pin 11' of timer IC2 as well as to one input of IC1/D. Output 50 of IC1/C is also connected via diode D7 to pin 11'. The output of IC1/A is connected to pin 10' of IC2.

I claim:

1. Salinity control means for the control of salinity of sump water of an evaporative cooler of the type wherein a pump continuously impels a water flow from a sump and through a conduit to be discharged over an evaporative surface where some water is evaporated by a flow of air from a fan, surplus water returning to the sump and evaporated water being replenished through a valve responsive to water level in the sump, said control means comprising:

resistance sensing electrical probes insertable within an evaporative cooler sump for detecting the electrical resistance of water in said sump, a solenoid actuated drain valve, an electronic drain valve control circuit electrically coupled to the solenoid of said drain valve and including a timer having an "ON" period and an "OFF" period, and control means for initiating said "ON" period upon electric resistance of water within the sump reducing below a preset level;

said electrical coupling operable for maintaining said drain valve open only during said "ON" period of said timer operations, said "OFF" period being initiated at the termination of each said operation "ON" period; and said drain valve control circuit also including a voltage regulator and an output pin which is initially "low" and comprising means for causing re-initiation of said timer "ON" period operation at termination of aforesaid "ON" period if said detected sump water electrical resistance is still below said preset level, said output pin going "high" and thereby inhibiting reinitiation if said sump water is above said preset level until termination of said "OFF" period.

2. Salinity control means according to claim 1 wherein said probes comprise a pair of monel metal electrodes projecting from a carrier.

3. Salinity control means according to claim 1 wherein said solenoid actuated drain valve comprises a conduit "T" junction with an upstream limb of the "T" junction being in direct fluid flow communication with an outlet part of a pump of said evaporative cooler a downstream limb of said "T" junction being in direct fluid flow communication with said evaporative surface, and a third limb of said "T" junction being in direct fluid flow communication with a drain conduit and containing a valve member, said solenoid being magnetically coupled to said valve member to open and close said third limb upon energizing and de-energizing of the solenoid.

4. Salinity control means according to claim 3 wherein said electronic drain valve control circuit comprises a conductivity sensing integrated circuit, said conductivity sensing integrated circuit having a very low voltage AC output, and probe conductors coupling said probes to said AC output.

5. Salinity control means according to claim 4, wherein said probe conductors comprise variable resistance devices which control said preset level upon which said timer initiation occurs.

6. Salinity control means according to claim 3, wherein said electronic drain valve circuit further comprises an integrated circuit which includes a multiple NOR gate occupied to and controlling said timer, an opto-isolator and a driver circuit, and an electronic power switch controlled by said driver circuit and in a power circuit of said solenoid.

* * * * *